United States Patent [19]
Rowley et al.

[11] Patent Number: 6,080,188
[45] Date of Patent: Jun. 27, 2000

[54] SETSCREW LESS LEAD CONNECTOR SYSTEM FOR MEDICAL DEVICES

[75] Inventors: George J. Rowley, Minnetonka; Gary M. Grose, Brookly Park; Brian R. Burwick, Clear Lake; Mitchell R. MacIver, Ramsey; Jane M DeMay, St. Louis Park, all of Minn.

[73] Assignee: Medtronic, Inc.

[21] Appl. No.: 08/877,033

[22] Filed: Jun. 16, 1997

[51] Int. Cl.[7] .................................................. A61N 1/375
[52] U.S. Cl. .................................................. 607/37; 607/36
[58] Field of Search ........................................ 607/36, 37

[56] References Cited

U.S. PATENT DOCUMENTS

| | | | |
|---|---|---|---|
| 4,154,248 | 5/1979 | Jones | 607/37 |
| 4,461,194 | 7/1984 | Moore . | |
| 4,860,750 | 8/1989 | Frey . | |
| 5,413,595 | 5/1995 | Stutz . | |
| 5,679,022 | 10/1997 | Cappa et al. | 607/27 |

FOREIGN PATENT DOCUMENTS 3718913  12/1988  Germany .................................. 607/37

*Primary Examiner*—William E. Kamm
*Assistant Examiner*—Carl H. Layno
*Attorney, Agent, or Firm*—Harold R. Patton; Michael B. Atlass

[57] ABSTRACT

A connector for clamping lead bodies into connector bores in implantable medical devices has several alternative embodiments. In each there is a handle that has a fixed relationship with an axle member that connects through the connector block perpendicular to the long axes of the connector bores for the leads. A large, manually operable flag or handle member clicks into position to lock the lead in by positioning a saddle portion against the lead body in the bore. The handle may be split into legs or the axle may be split into legs and the space between the legs filled with medical adhesive if desired. Likewise a soft material elastomer may surround the saddle portion to prevent rough contact with the lead body.

20 Claims, 6 Drawing Sheets

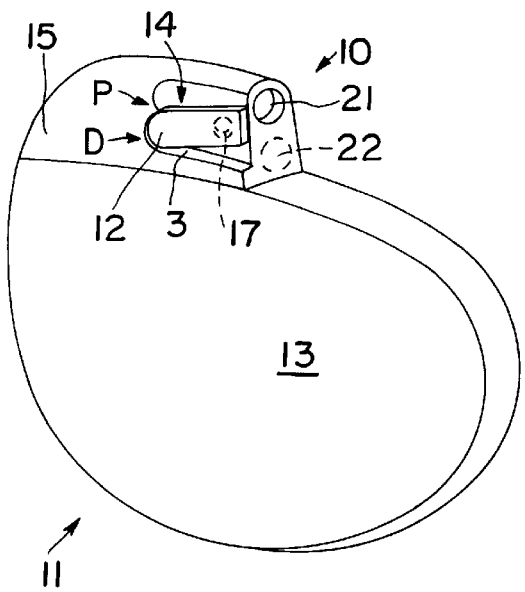
FIG. IA
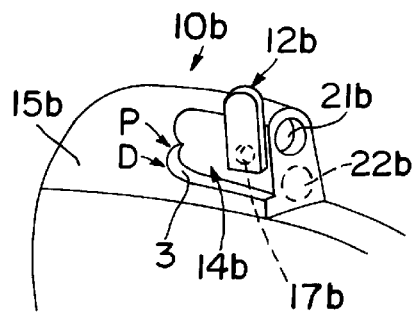
FIG. IB
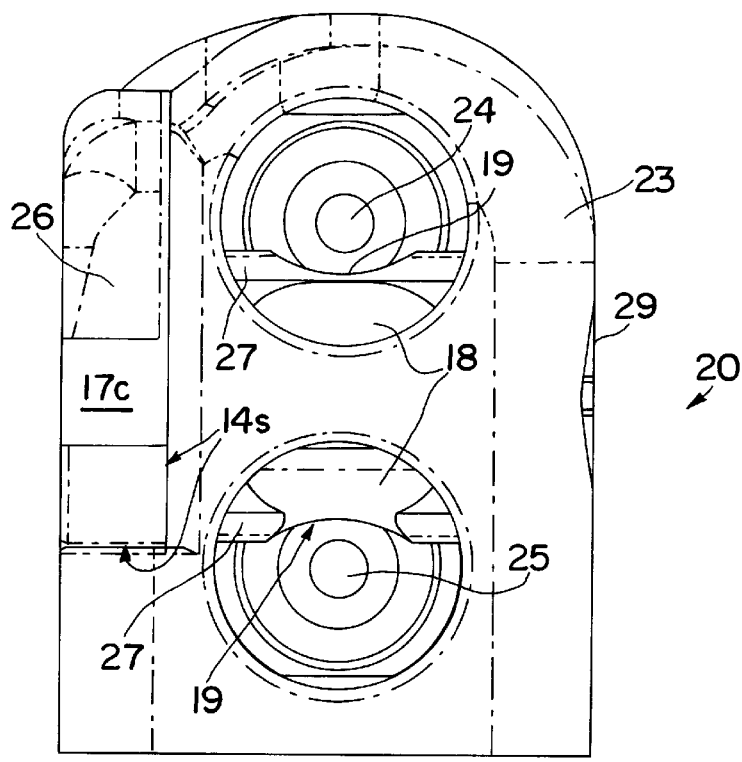
FIG. 2

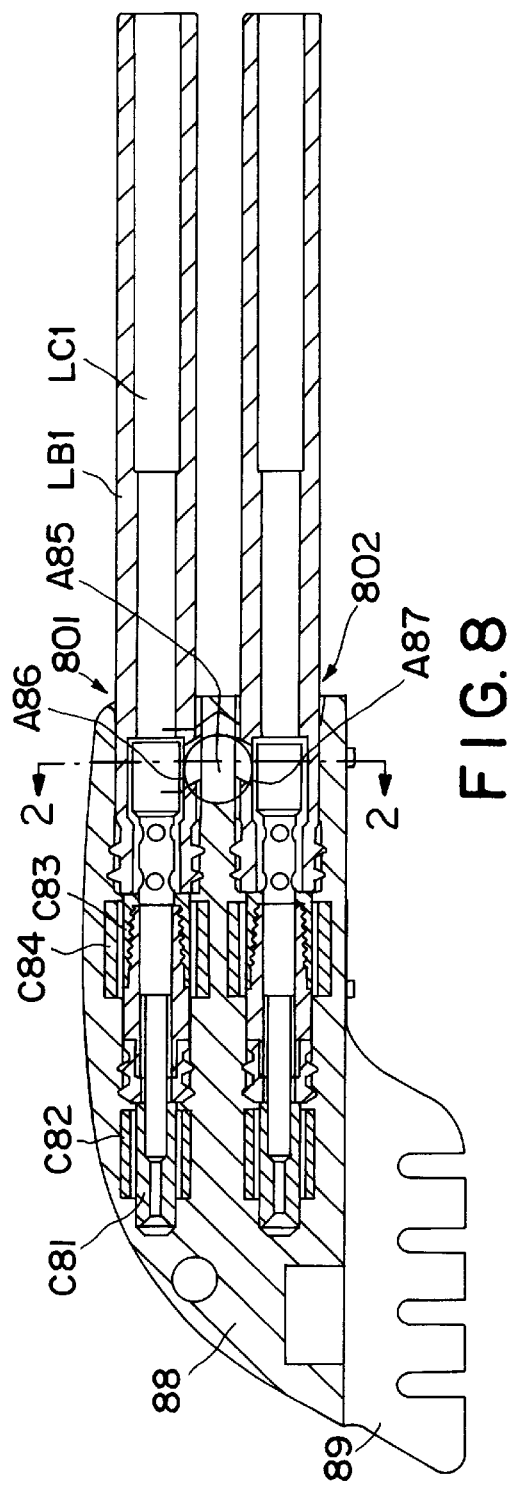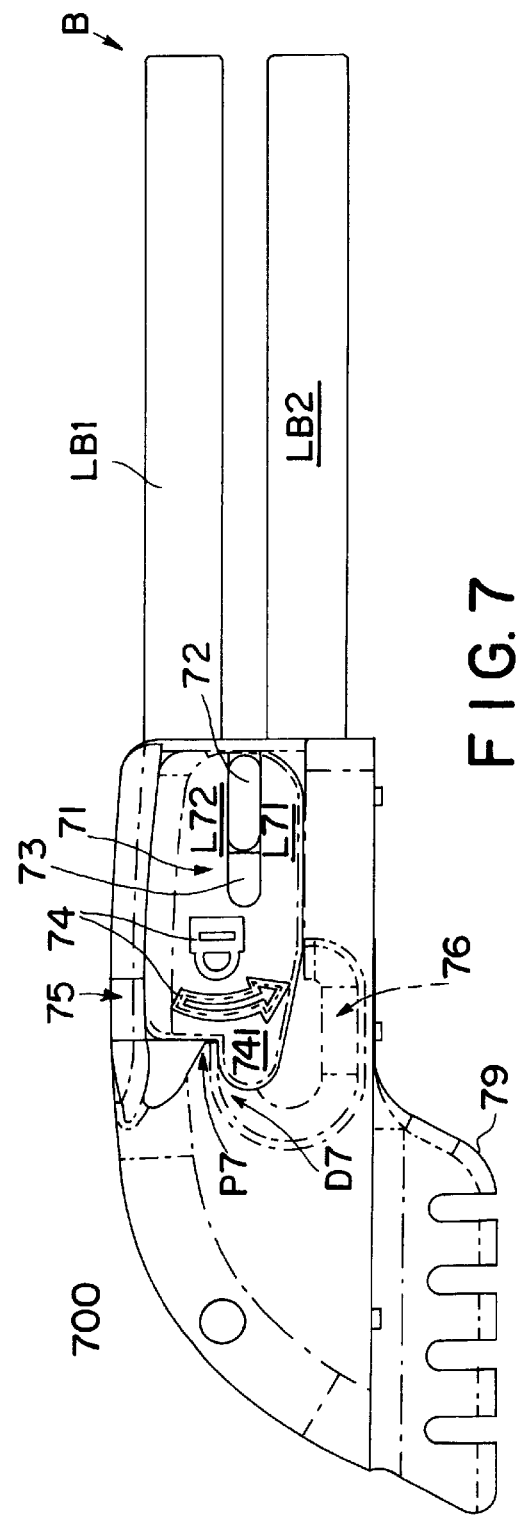

SETSCREW LESS LEAD CONNECTOR SYSTEM FOR MEDICAL DEVICES

FIELD OF THE INVENTION

This invention relates to connectors from medical leads particularly flexible leads having deformable lead bodies for connection by the application of pressure to the lead body when located in a less flexible connector block, and most particularly for medical electrical needs meeting the IS1 standard.

BACKGROUND

Due to the often life sustaining functions provided by implantable medical devices, a failure to maintain a positive connection between a lead which provides therapy to a body into which a device is implanted could be catastrophic. Accordingly the predominant concern in designing and implementing connector functions between medical leads and medical device bodies is to maintain firm and reliable locks on the connection between the parts.

Perhaps the most reliable mechanism to date is exemplified in U.S. Pat. No. 4,461,194 in which a tool such as a screw driver is used to rotatably urge a set screw against a lead body so that the lead body is deformed or maintained in position against a relatively undeformable bore. This set screw solution can also be adapted to provide electrical connection if the part of the lead to which the set screw is applied is metallic.

Numerous problems can arise with the use of tools in a operating room and the general feeling is the less that can go wrong the better. Over compression resulting in damage to lead bodies and connectors is one problem. The potential for lost of surgical instruments is another. Accordingly, tool less and setscrew less connecting systems will be preferred for implantable medical device connections to their leads if they are easy to use by a surgeon.

Two such Setscrew Less connector systems are seen in U.S. Pat. No. 4,860,750 issued to Frey et al, and U.S. Pat. No. 5,413,595 issued to Stutz. In the Frey patent a slideable wedge member locks into place around the lead body, this slideable member having the effect of urging the lead body against the relatively immovable bore wall opposite the slideable member surface. By urging the slideable member into place until it reaches a locked position the surgeon can feel a click against the lock mechanism. In the 750 patent it is a detent into which a protrusion attached to the slideable member falls and locks when the slideable member is fully in place. An alternative wedge member is described with reference to Frey's FIGS. 12 and 13 in which a rotatable wedging cam is oriented into position using a screw head 83.

An alternative means of compressing a lead body into a lead bore without resort tools is shown in the Stutz patent. Here a channel provides slideable access to two opposed cam surfaces which force together a sphincter seal around the lead body.

None of these cited references or any other provide the surgeon with both tactile and visual confirmation of the locked in place connector. Accordingly to facilitate the process of implanting medical devices having leads associated with them the applicant herein provides such a mechanism and system.

BRIEF DESCRIPTION OF THE DRAWINGS

FIG. 1a is a perspective view of a implantable medical device having mounted thereon a tools connector in accord with a preferred embodiment of this invention.

FIG. 1b is a perspective view similar to FIG. 1a but having the invention in an opened or unlocked position.

FIG. 2 is a head on view looking into the two bores of a connector block employing a preferred embodiment of this invention.

FIG. 7 is a side view of a locked connector block having two leads connected thereto in accord with a preferred embodiment.

FIG. 8 is a cross sectional view side view of the connector block of FIG. 7, viewed from the opposite side showing in FIG. 7.

SUMMARY OF THE INVENTION

Figure 3:
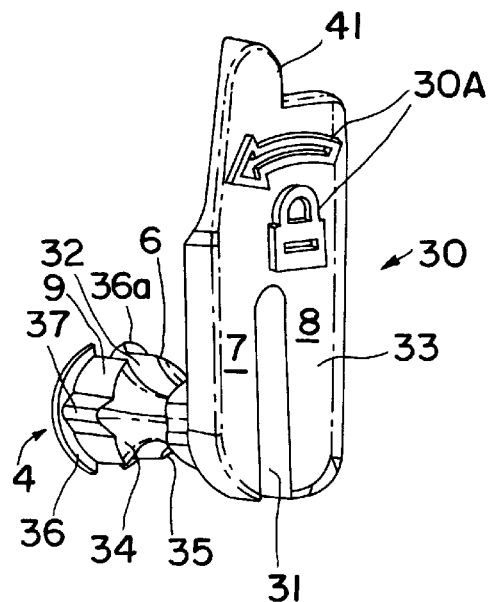
FIG. 3 is a perspective view of a handle and axle member for use in the preferred embodiment of this invention.

Setscrew Less Connector System for Implantable Medical Device is described having generally a lever handle member fixed to an axle member, the axle member for rotating within a sleeve running perpendicular to lead bore in a connector block. By the simple expedient of employing two identical pairs of surfaces on the axle exterior where it meets with the lead bore, a single sleeve employing the inventive handle and axle combination can operate to secure two leads at a single time. In either the single or double bore versions concave contoured surfaces are used to both compress and lock body when the axle is in one position, and to decompress the lead body or provide access to the lead bore hole in its other orientation.

In a preferred form a slot should run through the axle member so that this slot may be filled with a more elastomeric filler.

A pictographic of the functioning of the lock mechanism of the Setscrew Less connector maybe inscribed on the surface of the implantible medical device so as to facilitate the use of the locking mechanism.

DETAILED DESCRIPTION OF THE PREFERRED EMBODIMENT

Referring first to FIG. 1a, the connector block 10 is illustrated in perspective view to show the workings of the invention. Generally a connector block 15 is provided on implantable medical devices 13 to form a unit 11 so that a lead or leads may be inserted into a lead bore 21, or, if two bores 21 and 22, 22 being shown in ghost (or dotted line). A typical example would be a pacemaker using the lead bore to provide an electrical connection to a lead having a conductive pathway usually of a coiled metal wire within it to bring stimulus pulses to an organ in the body such as the heart and/or to receive measurements from said organ or other location within the body where the distal position or lead tip may be located. The connector block 15 has a cut out section 14 into which a handle member 12 maybe placed. Dotted circle 17 indicates the location of the axle member relative to the handle 12 in the illustration. As shown in FIG. 1*a* with the handle down and locked against a protruding surface P and in a detent surface D it rests close to a ledge 3. A space may be provided between the lever member and the ledge to allow for opening the lock. In a open position, illustrated in FIG. 1*b*, the handle member 12*b* is clear of the protrusion P and out of the detent D providing a fairly robust visual indication that the lead or is not closed. In these two illustrations a lead bore 21 and 21*b* are shown as are potential lead bores 22 and 22*b* which may be used as described further below. Again in FIG. 1*b* the location and orientation of the axle are shown by dotted circle 17*b*.

FIG. 2 provides a view of the locked inventive mechanism 20 looking face on into the connector bores, their centers located 24 and 25. The lever handle member here is illustrated by unit 26 and the axle's connection to it by 17*c*. The cut out area for the handle member in this view of this embodiments defined by the two lines 14*s*. Parallel surfaces 19 on the top and bottom of the axle member are close to the full diameter of the axle illustrated here as exterior surfaces 27. The perpendicular surface of the axle 18 and one on its opposite side but parallel to 18 (not shown ) has a deeper concave space or curvature that is less near to the outer diameter of the axle then the surfaces 19 just described. To visualize an arrangement of what this looks sort of like, one could consider the concave surfaces as corresponding very generally to four horse saddles connected to each other where the stirrups would be connected, wherein there are two identical pairs, one pair larger than the other and neither of which touches its twin in the arrangement around a circle, their seats portions all facing outward.

A flange or lip 29 or other mechanism can be provided to prevent the easy removal of the axle member from its sleeve or through hole(item 75 in FIG. 6, not seen in this drawing) in the connector block.

Referring to FIG. 3, the handle and axle assembly 30 is shown removed from the connector block. In the preferred embodiment the protrusion such as protrusion 41 will provide in large part the tactile sensation of a lockable clicking against a protrusion on the connector block such as P in FIGS. 1*a* and 1*b* when the assembly is locked. by being forced into detent D. For additional visual assurance a pictogram such as 30*a* can be provided showing an arrow indicating the direction in which a locking operation will be complete.

The preferred embodiment is not a simple solid handle mounted at a right angle to an axle, rather it has a number of features of importance to various aspects to this invention beyond the locking detent mechanism. One of these is provided by an open slot way illustrated here in the perspective drawing by a slot extending between arrow 31 and arrow 32. This effectively divides the handle mechanism into two arms 7 and 8 each connected to one side of the axle member, sides 9 and 6 respectively. The flange or lip member here is illustrated as lip member half's 36 and 36*a*. It can easily be seen that there is a protruding ridge 37 on side 9 which has an opposite member (not visible) on side 6 of the axle member. The portion of the axle member which engages the lead bore is area 35 here illustrated as a complex set of concave curved surface. A frontal view taken from the axle side just behind the lip 36 (not shown) shows protrusion 37 extending from the surface of side 9 and in addition how a pocket can be provided (39) if desired for further flexibility. Beveled or rounded edges like beveled edge 38 may be provided to the manually engagable segments of the handle portion 33*b* if desired. In fact any shape capable of enjoying the detent and protrusion to hold an axle in a locking position will suffice.

Figure 5:
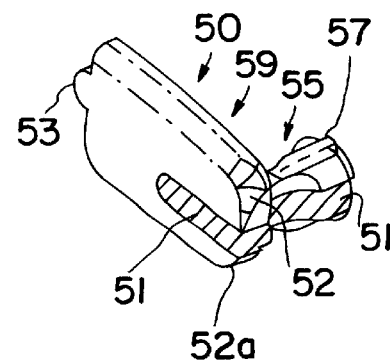
FIG. 5 is another perspective view of the preferred embodiment handle and axle of the invention.

In FIG. 5*a* similar embodiment of handle member 50 is shown again in perspective view with a lever handle member 59 associated perpendicularly with a axle member 55. A detent is employed here also and smooth corners are provided 52 and 52*a*. A medical epoxy or surgical filler is used to fill the space 51. By employing medical adhesive the two axle sides and the two lever handle legs are enabled to compress somewhat to allow the lip to fit through the axle sleeve for mounting into the sleeve. Additionally the added compressibility provides for a less damaging pressure against the lead body when it is locked in place.

To complete the description of the invention the bore into which the handle member must be inserted and the preferred sleeve into which the axle is mounted must be described. Also, it is to be noted that the handle is generally preferred to be built of a material of the same or slightly greater hardness than the connector block.

Figure 6:
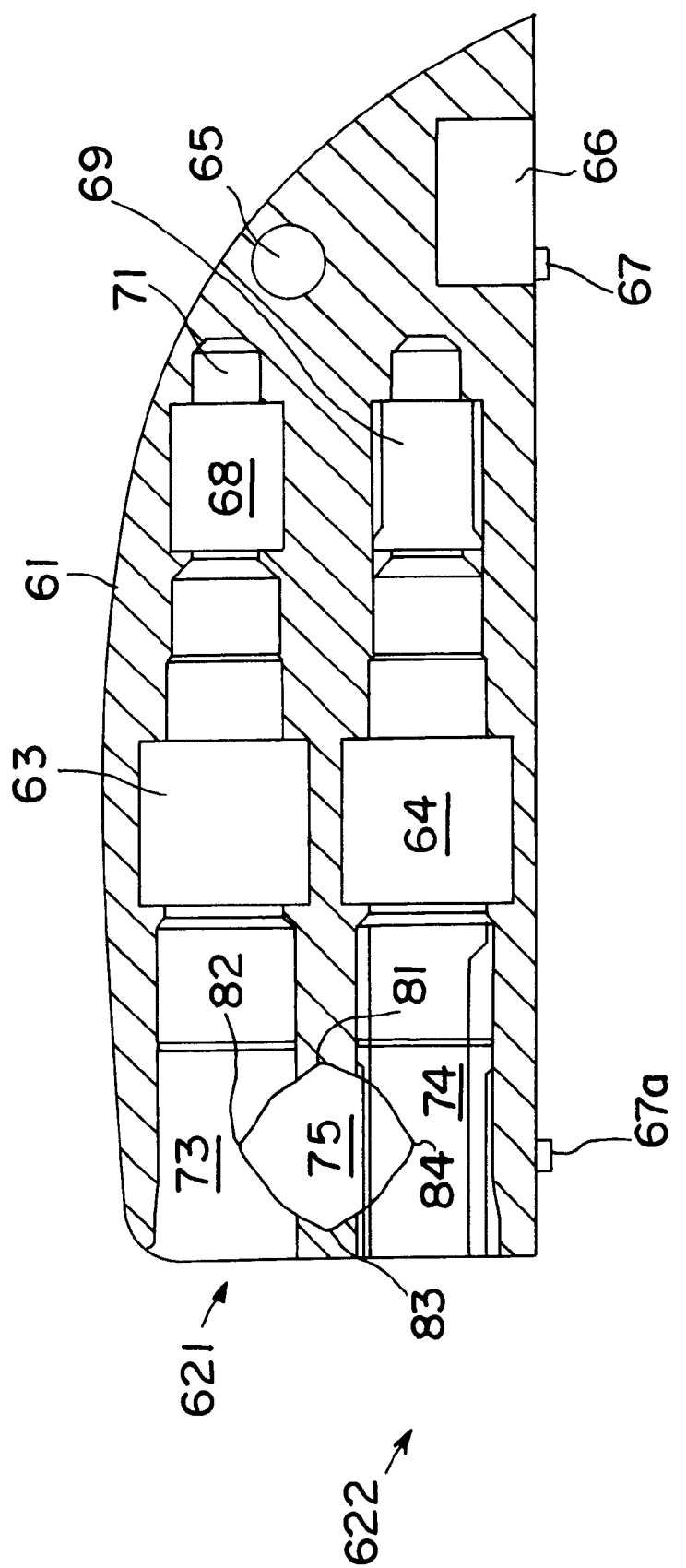
FIG. 6 is a cross sectional view of an empty connector block in accord with an and for use in a preferred embodiment of this invention.

Referring now to FIG. 6 in which a sleeve 75 is illustrated perpendicular to bores 621 and 622 in a hard plastic connector block 61 are shown in illustration 60. Cut out spaces within the lead bore 63, 64, 68 and 69 are provided for metallic members to contact metallic or conductive members of the lead when properly inserted in a manner common to the pacemaker art. Commonly, a solid metal end of the lead will extend all the way to ends or ends spaces 71 and 72. A suture hole 65 is often provided in connector blocks as are spaces 66 and extensions 67 and 67*a* for providing various functions such as radio opaque markers and fastening bumps or protrusions for secure connection of the connector block to the implantable medical device body. In this partial connector block illustration, no electrical connection between the features of the implantable medical device and the lead will be shown.

Figure 4:
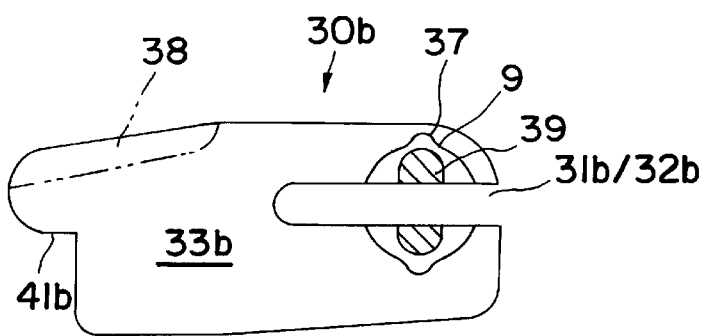
FIG. 4 is a front planner view taken from side four of FIG. 3 of the handle and axle of a preferred embodiment of the invention.

Importantly, their are four detents or corners 81–84 provided to the sleeve 75 into which the axle of the handle member will fit. These corners provide for secure connection to protrusions such that are illustrated 37 and 57 in FIGS. 3–5. Thus by turning the lever handle member from a down position to an up position there are two precise locations for the mating engagement of the protrusion members as the protrusions click into their corners, the person moving the lever handle as well as the snapping click in of the protrusion (4) into the detent D behind the protrusion P on the connector block.

Referring now to FIG. 7 the connector block 700 is seen with leads LB1 and LB2. The locking lever 71 provides for several indications of the secure lock, including the click felt when protrusions 741 snaps past protozoon P7 and to detent D7, the visual pictograph representation of the closed lock and arrow indicating the direction of closure of 74 at the sideways plug 72 which is matching the representation on the closed lock. The legs of the handle member L72 and L71 may additionally be filled in with medical adhesive or other suitable plastic at position 73.

An extended depression 76 is provided in the hard plastic connector block so that the lock maybe opened if required during surgery. For further ease of use and indention 75 can be provided in the connector block. Attached to this embodiment of the invention is a side guard 79 formed for extensively with the connector block so as to provide some additional stability in the connection of the connector block to the IPG shell and to provide additional protection to the wires which must be connected through feedthroughs in the shell to connecting electrodes associated with the leads now locked into the connector block.

In FIG. 8 a cut away of the connector block 800 is shown having two lead bores 801 and 802 extending most of the way there through. Again the preferable material for making the connector block 88 is hard plastic and the addition of a feedthrough wire guard and stabilizing member 89 is also illustrated here. The section through the axle is indicated here by a circle surrounding the point A 85. Compression of the lead bodies takes place in area A86 and A87. The electrical connection of the lead to the electrical connectors in the IPG's connector block 800 is accomplished by mating contact of the electrical contacts C81 and C82 and C83 and C84. Not shown in this drawings are the connections within the lead itself from connectors C81 and C83 to wires that extend through the lead cavity LC1 to the lead distal end of lead body LB1, said end also not shown.

Figure 9:
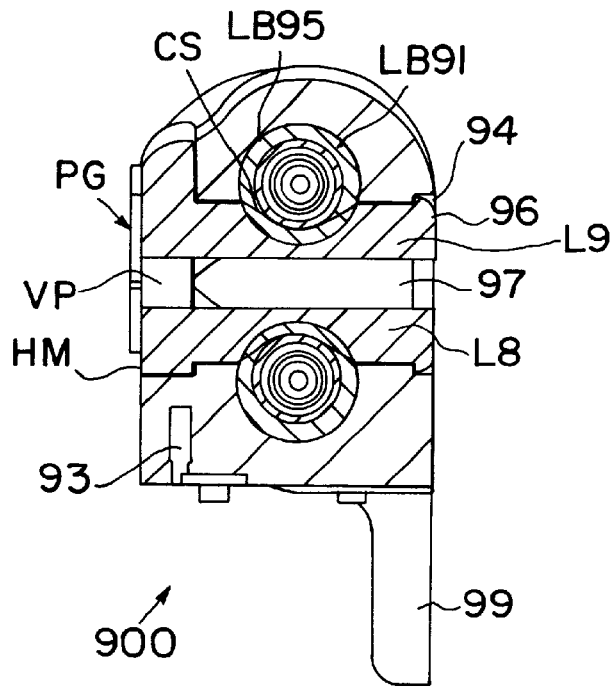
FIG. 9 is a front sectional view of the lead bodies sectional along with the section of the connector block taken at lines B—B of FIG. 8.

In FIG. 9, a section is taken of a connector block 900 having lead bodies like LB91 inserted therein. Lead bore perimeter is identified by LB95. Thus when the axles curved surface CS is moved into position by the handle mechanism connected to it HM the lead body LB1 is compressed against the side of the bore LB95 opposite curve surface CS. Again, by including a spongy or elastomeric material like medical adhesive in the space 97 the legs L9 and L8 may flex and thus the surface CS need not deform the lead body LB91 in a damaging matter.

Figure 10A:
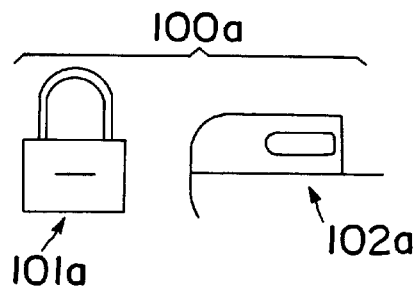
FIGS. 10a, b, and c, illustrate an instructional pictograph for engraving onto a IPG surface to avoid confusion in use of this invention in an operating room during implant.
Figure 10B:
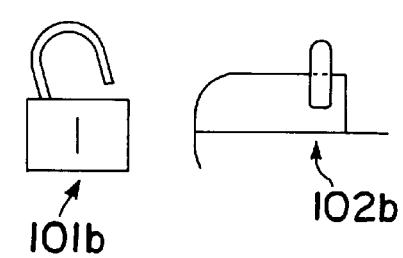
Figure 10C:
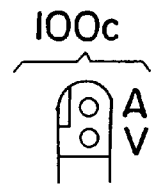

As with any innovation, the use of international pictographic information to assure its safe operation can be provided as illustrated in FIGS. 10a–c in FIG. 10a two symbols 101A and 102A are illustrated in the pictogram 100A. Thus when the handle in 102A is down the lock in 101A is closed. In FIG. 10b, the pictogram is represented by elements 101B and 102B. Here the lock 101B is illustrated in a open position as is the handle in 102B. For double bore connector blocks illustration FIG. 10c may be appropriate having a pictogram 100C showing which bore is for the Atrial lead and which bore is for the Ventricular lead if the connector block is used in a pacemaker.

Figure 11:
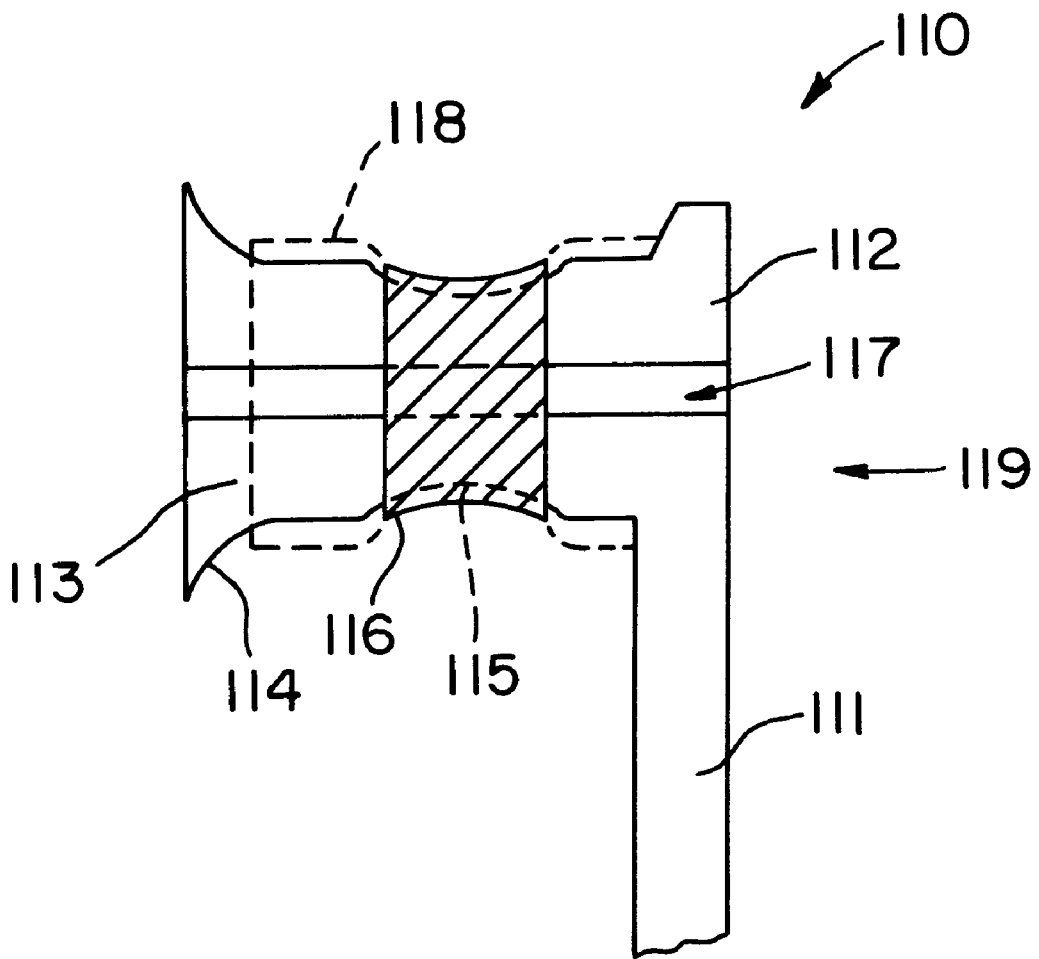
FIG. 11 is a partial side view of an alternative embodiment also constructed in accord with this invention in accord with this invention.

An alternative embodiment for this invention's handle is shown in FIG. 11, in which a part of the handle member 111 of the handle 110 formed contiguously with the axle member 119. In one embodiment the axle member has a through portion 117 which may be open or filled with a soft elastomeric material or filled in as desired, between the two leg members 113 and 112. A ring or sleeve of soft elastomeric plastic latex or rubber material sits on the curve 115 of the saddle portion of the axle 119. This may extend across the entire portion of the axle as illustrated by dotted line 118 or, preferrably, be located just over the saddle portion as illustrated material member 116 is drawn. In all these alternate embodiments the relatively hard plastic on the handle 110 and it's effect on the soft body of a lead pressed against the saddle portion of the axle 119 will be ameliorated by the softness of the sleeve 115's material composition, thus allowing for easier compliance with the IS1 standard for leads and more lead compatibility with leads of different manufacturers. Preferably where the softer material coats the saddle portion, it generally follows the curve of the saddle portion, although if it is very soft, that may not be necessary.

The implications for the use of this invention should be apparent to one of ordinary skill in the art. Many additional features and obvious variations of the illustration may occur to the reader but however should be considered within the ambit of this invention unless excluded by the following appended claims.

What is claimed:

1. A handle unit for use in an implantable medical device with a base for connecting said implantable medical device to a lead body end, said handle for use by direct manual operation to close off and open to lead access and engagement in said bore, said handle unit comprising;

an axle member for turnable engagement with said lead body, said axle member having at least two longitudinal portions forming a substantial part of said axle member, a first outer surface area of said substantial part being of a smaller radial dimension than a second outer surface area of said substantial part which is disposed circumferencially from said first outer surface and, a manually engageable handle member for imparting rotational movement to said axle member substantial part having a manually engageable lever handle member in fixed engagement with said axle member longitudinal portion, such that when movement in an arc is imparted to said lever handle member rotational movement of said axle member is imparted in the same degree and direction about a central axis of said substantial part.

2. An implantable medical device having a pictogram exhibited on the surface thereof, illustrating the use of a handle as set forth in claim 1 in a connector block.

3. A connector block for use by fixation to an implantable medical device such that an electrical connection between a circuit in an implantable medical device and electrode in a medical lead is establishable by insertion of said medical electrical lead into a lead bore in said connector block and wherein said lead bore has a long axis, said connector block comprising a hard plastic block with a sleeve formed therein said sleeve adapted for insertion of a handle actuated rotatable axle thereinto and having a through-axis substantially perpendicular to said lead bore long axis having a handle as set forth in claim 1 mounted therein so that said axle member substantial part is located in said sleeve.

4. A handle as set forth in claim 3 wherein material of which said handle is formed of material of a different hardness than material of which said connector block is formed.

5. A handle as set forth in claim 1 wherein said axle member has a saddle portion outer surface for mating with a lead body in compressed relation.

6. A handle as set forth in claim 5 wherein said saddle portion has a soft material coating said outer surface.

7. A handle member as set forth in claim 1 wherein said substantial part of said axle member second surface comprises a part of a saddle portion outer surface for mating with a lead body in compressed relation.

8. A handle member as set forth in claim 7 wherein said axle member saddle portion outer surface and said axle leg portions have a soft material coating thereon.

9. A handle unit as set forth in claim one wherein said handle member has a top portion and two leg portions each of said leg portions connected to one of said longitudinal portions of said axle member substantial part.

10. A handle as set forth in claim 9 wherein a soft elastomeric material substantially fills a space between said longitudinal portions.

11. A handle as set forth in claim 9 wherein a soft elastomeric material substantially fills a space between said legs portions.

12. A handle as set forth in claim 10 having a pictographic representation of its function exhibited thereon.

13. A handle as set forth in claim 10 having a visible directional indicator located between said leg portions of said handle member.

14. A handle as set forth in claim 10 having a visible directional indicator located on said top portion of said handle member.

15. A handle member as set forth in any one of claims 5–8 wherein said softer material has an outer surface that follows the curve of the outer surface of said saddle member.

16. A connector block for use by fixation to an implantable medical device such that an electrical connection between a circuit in an implantable medical device and electrode in a medical lead is establishable by insertion of said medical electrical lead into a lead bore in said connector block and wherein said lead bore has a long axis, said connector block comprising a hard plastic block with a sleeve like cavity formed therein, said sleeve like cavity adapted for and having inserted thereinto a handle actuated rotatable axle and having a through-axis substantially parallel to said inserted axle and substantially perpendicular to said lead bore long axis, and wherein said handle is sufficiently large for manual use and permanently affixed to said rotatable axle.

17. A connector block for use by fixation to an implantable medical device such that an electrical connection between a circuit in an implantable medical device and electrode in a medical lead is establishable by insertion of said medical electrical lead into a lead bore in said connector block and wherein said lead bore has a long axis, said connector block comprising a hard plastic block with a sleeve like cavity formed therein said sleeve like cavity adapted for insertion of a handle actuated rotatable axle thereinto and having a through-axis substantially perpendicular to said lead bore long axis wherein said sleeve like cavity has a substantially round passage therethrough but has four corner-like detents in a substantially square configuration arranged around said substantially round passage.

18. An implantable medical device having a connector block and handle mounted therein such that said handle imparts mechanical movement to an axle member fixed thereto, said axle member being mounted in said connector block perpendicularly across a lead bore formed in said connector block, and such that said handle in a position for providing locking connection between said medical device to medical electrical leads is locked by manual movement of a portion of the handle behind a detent formed in said connector block.

19. A method for operatively coupling a medical electrical lead to a connector block of an implantable medical device comprising;

inserting a connector end of said medical electrical lead into a lead bore in said connector block, manually imparting rotational movement to a lever handle to turn an axle so as to more tightly engage said medical electrical lead in said connector block bore by rotating a larger diametered portion of said axle into tight engagement with the lead.

20. A method as set forth in claim 19 further comprising;

manually locking said lever handle into a detent area in said connector block so as to lock said larger diametered portion of said axle into tight engagement with said medical electrical lead.

* * * * *

UNITED STATES PATENT AND TRADEMARK OFFICE
CERTIFICATE OF CORRECTION

PATENT NO. : 6,080,188  
DATED : June 27, 2000  
INVENTOR(S) : Rowley et al.

Page 1 of 1

It is certified that error appears in the above-identified patent and that said Letters Patent is hereby corrected as shown below:

Column 7, claim 13,
Line 4, "claim 10" should read -- claim 3 --
Line 4, "located between said leg portions" should read -- located on said top portion --

Signed and Sealed this

Eighteenth Day of December, 2001

Attest:

Attesting Officer

JAMES E. ROGAN
Director of the United States Patent and Trademark Office